(12) United States Patent
Morishita et al.

(10) Patent No.: US 10,675,242 B2
(45) Date of Patent: Jun. 9, 2020

(54) AQUEOUS FORMULATION CONTAINING 5-AMINOLEVULINIC ACID OR THE LIKE

(71) Applicant: SBI PHARMACEUTICALS CO., LTD., Tokyo (JP)

(72) Inventors: Mika Morishita, Hyogo (JP); Urara Ota, Hyogo (JP); Masahiro Ishizuka, Tokyo (JP)

(73) Assignee: SBI PHARMACEUTICALS, CO., LTD., Tokyo (JP)

( * ) Notice: Subject to any disclaimer, the term of this patent is extended or adjusted under 35 U.S.C. 154(b) by 0 days.

(21) Appl. No.: 16/326,733

(22) PCT Filed: Aug. 23, 2017

(86) PCT No.: PCT/JP2017/030107
§ 371 (c)(1),
(2) Date: Feb. 20, 2019

(87) PCT Pub. No.: WO2018/043240
PCT Pub. Date: Mar. 8, 2018

(65) Prior Publication Data
US 2019/0201336 A1 Jul. 4, 2019

(30) Foreign Application Priority Data

Sep. 2, 2016 (JP) .................... 2016-171753

(51) Int. Cl.
| | | |
|---|---|---|
| *A61K 9/08* | (2006.01) | |
| *A61K 47/02* | (2006.01) | |
| *A61K 31/197* | (2006.01) | |
| *A61K 47/12* | (2006.01) | |
| *A61K 31/22* | (2006.01) | |
| *A61K 9/06* | (2006.01) | |
| *A61K 31/295* | (2006.01) | |

(52) U.S. Cl.
CPC ................. *A61K 9/08* (2013.01); *A61K 9/06* (2013.01); *A61K 31/197* (2013.01); *A61K 31/22* (2013.01); *A61K 31/295* (2013.01); *A61K 47/02* (2013.01); *A61K 47/12* (2013.01)

(58) Field of Classification Search
CPC .......... A61K 9/06; A61K 9/08; A61K 31/197; A61K 31/22; A61K 31/295; A61K 47/02; A61K 47/12
See application file for complete search history.

(56) References Cited

U.S. PATENT DOCUMENTS

| | | | |
|---|---|---|---|
| 2003/0065029 A1 | 4/2003 | Tanaka et al. | |
| 2013/0011337 A1* | 1/2013 | Kuroiwa | A61K 31/197 424/9.6 |
| 2014/0288173 A1 | 9/2014 | Tanaka et al. | |
| 2014/0302173 A1 | 10/2014 | Tanaka et al. | |
| 2014/0343140 A1 | 11/2014 | Tanaka et al. | |
| 2017/0056351 A1 | 3/2017 | Nishizawa et al. | |

FOREIGN PATENT DOCUMENTS

| | | |
|---|---|---|
| CN | 105878225 | 8/2016 |
| JP | H08175986 | 7/1996 |
| JP | H1112197 | 1/1999 |
| JP | 2001518498 | 10/2001 |
| JP | 2010/095479 | 4/2010 |
| JP | 2011016753 | 1/2011 |
| WO | 2015/129535 | 9/2015 |

OTHER PUBLICATIONS

Written Opinion and International Search Report corresponding to International Patent Application No. PCT/JP2017/030107, dated Nov. 21, 2017, 8 pages, Translation.

* cited by examiner

*Primary Examiner* — Joseph R Kosack
(74) *Attorney, Agent, or Firm* — Myers Bigel, P.A.

(57) ABSTRACT

The object of the invention is to elevate the stability of an aqueous formulation comprising ALAs and an iron compound. The present invention provides an aqueous formulation comprising ALAs and an iron compound, characterized in that it further comprises 0.2-30% by weight of salts, said salts are sodium salts or potassium salts, and the pH of said aqueous formulation is 2-8.

9 Claims, 9 Drawing Sheets

AQUEOUS FORMULATION CONTAINING 5-AMINOLEVULINIC ACID OR THE LIKE

STATEMENT OF PRIORITY

This application is a 35 U.S.C. § 371 national phase entry of International Application Serial No. PCT/JP2017/030107, filed Aug. 23, 2017, which claims the benefit under 35 U.S.C. § 119(a) of Japanese Patent Application No. 2016-171753, filed Sep. 2, 2016, the disclosure of each of which is incorporated herein by reference in its entirety.

TECHNICAL FIELD

The present invention relates to an aqueous formulation comprising 5-aminolevulinic acids (hereinafter also referred to as "ALAs") with improved stability.

BACKGROUND ART 5-aminolevulinic acid (hereinafter also referred to as "ALA") is a type of natural amino acid comprised in vivo that exists widely in animals or plants or fungi, and is metabolized in cells as a common precursor of chlorophyll or heme. Although ALA, similarly to other porphyrin-related compounds, has the nature to selectively accumulate in tumor tissues, it does not itself possess light sensitivity, but becomes light sensitive protoporphyrin IX (hereinafter also referred to as "PpIX") by being metabolized by a series of enzymes in the heme biosynthetic pathway in cells.

Research on 5-aminolevulinic acid—photodynamic therapy (hereinafter also referred to as "ALA-PDT") or 5-aminolevulinic acid—photodynamic diagnosis (hereinafter "ALA-PDD") that utilize the above nature of ALA and a metabolic product thereof PpIX has been brought forward (e.g. Patent Literature 1). Cancer therapy by ALA-PDT is a therapeutic method of treating cancer by administering ALA to a subject and irradiating light of a particular wavelength to the cancer tissue, is a therapeutic method that is minimally invasive and has less chance of leaving a therapeutic scar, and therefore has been gathering attention in recent years. ALA-PDD is a diagnostic method of determining the presence or absence of cancer tissue and the range of cancer tissue by administering ALA to a subject and irradiating light of a particular wavelength to the cancer tissue, is minimally invasive and has less side effects compared to prior diagnostic methods, and therefore has the advantage of having less burden on patients.

Further, it is known that a composition comprising ALA may be utilized for various applications such as prevention and alleviation of side effects of anticancer agents (Patent Literature 2), prevention and improvement of hangovers (Patent Literature 3), and prevention and improvement of cancerous anemia (Patent Literature 4).

CITATION LIST

[Patent Literature 1] Japanese Published Unexamined Patent Application Publication No. H11-12197
[Patent Literature 2] WO2013/054756
[Patent Literature 3] WO2013/084816
[Patent Literature 4] WO2013/054770

SUMMARY OF THE INVENTION

Problems to be Solved by the Invention

While developing a formulation comprising ALAs, the present inventors encountered a problem that when ALAs and an iron compound coexist in a formulation comprising water, the stability of ALAs in the formulation declines and the concentration of ALA decreases in a short period of time.

Means for Solving the Problems

As a result of extensive investigation by the present inventors in order to elevate the stability of an aqueous formulation comprising ALAs, it was surprisingly found that the stability of ALAs in the formulation is improved by adding given salts to an aqueous formulation comprising ALAs and an iron compound, thereby coming to complete the present invention.

In other words, in one embodiment, the present invention relates to an aqueous formulation comprising a compound shown by the following Formula (I):

[Chemical Formula 1]

(in which $R^1$ represents a hydrogen atom or an acyl group, and $R^2$ represents a hydrogen atom, a linear or branched alkyl group, a cycloalkyl group, an aryl group, or an aralkyl group) or a salt thereof and
an iron compound, characterized in that it
further comprises 0.2-30% by weight of salts,
said salts are sodium salts or potassium salts, and
the pH of said aqueous formulation is 2-8.

Moreover, one embodiment of the present invention is characterized in that in said Formula (I), $R^1$ is selected from the group consisting of a hydrogen atom, an alkanoyl group having 1-8 carbons, and an aroyl group having 7-14 carbons, and $R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

Moreover, one embodiment of the present invention is characterized in that in said Formula (I), $R^1$ and $R^2$ are hydrogen atoms.

Moreover, one embodiment of the present invention is characterized in that the ratio between the amount of said iron compound (mol) and the amount of the compound shown by said Formula (I) (mol) (iron compound/the compound shown by Formula (I)) contained in said aqueous formulation is 0.01-100.

Moreover, one embodiment of the present invention is characterized in that said sodium salt is sodium chloride, sodium sulfate, sodium carbonate, or sodium acetate, and said potassium salt is potassium chloride, potassium acetate, or potassium carbonate.

Moreover, one embodiment of the present invention is characterized in that said iron compound is one or two or more compounds selected from the group consisting of ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron sodium succinate citrate, heme iron, iron dextran, triethylenetetramine iron, lactoferrin iron, transferrin iron, sodium iron chlorophyllin, ferritin iron, saccharated iron oxide, and iron glycine sulfate.

Moreover, one embodiment of the present invention is characterized in that the pH of said aqueous formulation is 4-7.5.

Moreover, one embodiment of the present invention is characterized in that the pH of said aqueous formulation is 5-7.

Moreover, one embodiment of the present invention is characterized in that said aqueous formulation is in a form of an aqueous solution, a jelly, a gel, a cream, or an ointment.

Note that an invention of any combination of one or more characteristics of the present invention described above is also encompassed by the scope of the present invention.

DESCRIPTION OF EMBODIMENTS

ALAs as used herein refer to an ALA or a derivative thereof, or salts thereof.

ALA as used herein means a 5-aminolevulinic acid. ALA is also referred to as δ-aminolevulinic acid, and is a type of amino acid.

The compound represented by the following Formula (I) can be exemplified as an ALA derivative. In Formula (I), $R^1$ represents a hydrogen atom or an acyl group, and $R^2$ represents a hydrogen atom, a linear or branched alkyl group, a cycloalkyl group, an aryl group, or an aralkyl group.

Note that in Formula (I), ALA corresponds to when $R^1$ and $R^2$ are hydrogen atoms.

[Chemical Formula 2]

ALAs may act as an active ingredient in vivo in the form of the ALA of Formula (I) or a derivative thereof, and can also be administered as a prodrug (precursor) that is degradated by an in vivo enzyme.

The acyl group in $R^1$ of Formula (I) can include a linear or branched alkanoyl group having 1-8 carbons such as formyl, acetyl, propionyl, butyryl, isobutyryl, valeryl, isovaleryl, pivaloyl, hexanoyl, octanoyl, and benzylcarbonyl groups, or an aroyl group having 7-14 carbons such as benzoyl, 1-naphthoyl, and 2-naphthoyl groups.

The alkyl group in $R^2$ of Formula (I) can include a linear or branched alkyl group having 1-8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of Formula (I) can include a cycloalkyl group having 3-8 carbons which may be saturated or have partially unsaturated bonds, such as cyclopropyl, cyclobutyl, cyclopentyl, cyclohexyl, cycloheptyl, cyclooctyl, cyclododecyl, and 1-cyclohexenyl groups.

The aryl group in $R^2$ of Formula (I) can include an aryl group having 6-14 carbons such as phenyl, naphthyl, anthryl, and phenanthryl groups.

The aralkyl group in $R^2$ of Formula (I) can be exemplified with the same aryl groups as above as the aryl moiety and the same alkyl groups as above as the alkyl moiety, and can specifically include an aralkyl group having 7-15 carbons such as benzyl, phenethyl, phenylpropyl, phenylbutyl, benzhydryl, trityl, naphthylmethyl, and naphthylethyl groups.

Preferred ALA derivatives include compounds where $R^1$ is a formyl group, an acetyl group, a propionyl group, a butyryl group, and the like. Moreover, preferred ALA derivatives also include compounds where the above $R^2$ is a methyl group, an ethyl group, a propyl group, a butyl group, a pentyl group, and the like. Moreover, preferred ALA derivatives also include compounds where the combination of the above $R^1$ and $R^2$ is each combination of (formyl and methyl), (acetyl and methyl), (propionyl and methyl), (butyryl and methyl), (formyl and ethyl), (acetyl and ethyl), (propionyl and ethyl), and (butyryl and ethyl).

Among ALAs, a salt of an ALA or a derivative thereof can include a pharmaceutically acceptable acid addition salt, a metal salt, an ammonium salt, an organic amine addition salt, and the like. Acid addition salts can be exemplified by e.g. each of inorganic acid salts such as a hydrochloride salt, a hydrobromide salt, a hydroiodide salt, a phosphate salt, a nitrate salt, and a sulfate salt, and each of organic acid addition salts such as a formate salt, an acetate salt, a propionate salt, a toluenesulfate salt, a succinate salt, an oxalate salt, a lactate salt, a tartrate salt, a glycolate salt, a methanesulfonate salt, a butyrate salt, a valerate salt, a citrate salt, a fumarate salt, a maleate salt, and a malate salt. Metal salts can be exemplified by each of alkali metal salts such as a lithium salt, a sodium salt, and a potassium salt, each of alkaline earth metal salts such as a magnesium salt and a calcium salt, and each of metal salts such as aluminum and zinc. Ammonium salts can be exemplified by alkyl ammonium salts and the like such as an ammonium salt and a tetramethylammonium salt. Organic amine salts can be exemplified by each of salts such as a triethylamine salt, a piperidine salt, a morpholine salt, and a toluidine salt. Note that these salts can also be employed as a solution at the time of use.

Among the above ALAs, the most favorable are ALA and various esters such as an ALA methyl ester, an ALA ethyl ester, an ALA propyl ester, an ALA butyl ester, and an ALA pentyl ester, as well as hydrochloride salts, phosphate salts, and sulfate salts thereof. In particular, ALA hydrochloride salts and ALA phosphate salts can be exemplified as particularly favorable.

The above ALAs can be manufactured by e.g. well-known methods such as chemical synthesis, production by microorganisms, and production by enzymes. Moreover, the above ALAs may also form a hydrate or a solvate, and ALAs can be employed alone or in an appropriate combination of two or more.

The concentration range of the ALAs contained in the aqueous formulation of the present invention is not particularly limited, and can be appropriately selected by those skilled in the art. Generally, The dosage of ALAs for adults can include 0.01 mmol-25 mmol/day, preferably 0.025 mmol-7.5 mmol/day, more preferably 0.075 mmol-5.5 mmol/day, and further preferably 0.2 mmol-2 mmol/day, when converted into mols of ALA. By back calculation from these favorable dosages, the concentration range of ALAs contained in the aqueous formulation of the present invention can be determined. For example, the concentration range of ALAs contained in the aqueous formulation of the present invention may be 0.005% by weight-30% by weight, preferably 0.01% by weight-15% by weight, and further preferably 0.1% by weight-10% by weight.

Examples of the iron compound in the present invention can include e.g. ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron sodium succinate citrate, heme iron, iron dextran, triethylenetetramine iron, lactoferrin iron, transferrin iron, sodium iron chlorophyllin, ferritin iron, saccharated iron oxide, and iron glycine sulfate. Moreover, the aqueous formulation of the present invention may comprise one or two or more from the iron compounds exemplified above.

The concentration range of the iron compound contained in the aqueous formulation of the present invention is not particularly limited, and can be appropriately selected by those skilled in the art. Generally, the ratio between the amount of said iron compound (mol) and the amount of the compound shown by said Formula (I) (mol) (iron compound/the compound shown by Formula (I)) contained in the aqueous formulation of the present invention is preferably 0.01-100 (preferably). By back calculation from these favorable dosages, the concentration range of the iron compound contained in the aqueous formulation of the present invention can be determined. For example, the concentration range of the iron compound contained in the aqueous formulation of the present invention may be 0.01% by weight-30% by weight, preferably 0.05% by weight-15% by weight, and further preferably 0.1% by weight-10% by weight.

The aqueous formulation of the present invention is characterized in that it comprises salts. Examples of salts employed in the present invention can include e.g. sodium salts, potassium salts, magnesium salts, zinc salts, iron salts, lithium salts, calcium salts, copper salts, and ammonium salts, and in particular sodium salts or potassium salts can be favorably employed. Examples of sodium salts that may be employed in the present invention can include sodium chloride, sodium sulfate, sodium carbonate, and sodium acetate. Moreover, examples of potassium salts that may be employed in the present invention can include potassium chloride, potassium acetate, and potassium carbonate. Moreover, examples of other salts that may be employed in the present invention can include magnesium chloride, zinc chloride, magnesium sulfate, lithium chloride, calcium chloride, copper sulfate (II), zinc sulfate, iron sulfate (II), lithium acetate, ammonium acetate, and the like.

The concentration of salts contained in the aqueous formulation of the present invention is in the range of about 0.2-30% by weight. When the concentration of salts contained in the aqueous formulation becomes 0.2% by weight or less, it will become difficult to obtain the desired ALA stabilization effect, and when the concentration of salts contained in the aqueous formulation becomes 30% by weight or more, there is a risk that the concentration of salts will become too high, thus causing problems for use as a formulation. The preferred concentration range will vary depending on the type of salts, and those skilled in the art will be able to appropriately adjust the suitable concentration within the range of about 0.2-30% by weight, and for example can adjust to the range of about 0.2-25% by weight, about 0.2-20% by weight, about 0.2-18% by weight, about 0.2-15% by weight, about 0.8-25% by weight, about 0.8-20% by weight, about 0.8-18% by weight, about 0.8-15% by weight, about 1-25% by weight, about 1-20% by weight, about 1-18% by weight, about 1-15% by weight, about 2.5-25% by weight, about 2.5-20% by weight, about 2.5-18% by weight, about 2.5-15% by weight, about 5-25% by weight, about 5-20% by weight, about 5-18% by weight, or about 5-15% by weight. For example, when a sodium salt is employed, it is preferred that the concentration range is about 0.2-20% by weight, and when a potassium salt is employed, it is preferred that the concentration range is about 5-25% by weight. Further, when sodium chloride is employed, it is preferred that the concentration range is about 0.2-20% by weight, when sodium sulfate is employed, it is preferred that the concentration range is about 0.8-18% by weight, and when potassium chloride is employed, it is preferred that the concentration range is about 5-25% by weight.

Note that it is preferred that the "iron compound" and the "salts" contained in the aqueous formulation of the present invention are different.

An aqueous formulation as used herein broadly means a formulation that comprises water as the base. Examples of the form of the aqueous formulation in the present invention include, but are not limited to, a form of an aqueous solution, a jelly, a gel, a cream, or an ointment.

In addition to said ingredients, the aqueous formulation of the present invention may contain additives as necessary, such as a tonicity agent, a solubilizer, a viscous base, an algefacient, a pH adjusting agent, a preservative, a stabilizer, and a surfactant.

Examples of a tonicity agent include sugars such as sorbitol, glucose, and mannitol; polyvalent alcohols such as glycerin and propylene glycol; salts such as sodium chloride; boric acid, and the like. These tonicity agents may be used alone or in a combination of two or more.

Examples of a solubilizer include nonionic surfactants such as polyoxyethylene sorbitan monooleate, polyoxyethylene hydrogenated castor oil, tyloxapol, and Pluronic; polyvalent alcohol such as glycerin, and the like. These solubilizers may be used alone or in a combination of two or more.

Examples of a viscous base include water-soluble polymers such as polyvinylpyrrolidone, polyethylene glycol, polyvinyl alcohol, carboxyvinyl polymer, chondroitin sulfate ester sodium, alginic acid or a salt thereof, and sodium hyaluronate; celluloses such as hypromellose, hydroxyethyl cellulose, methyl cellulose, hydroxypropylcellulose, hydroxypropyl methyl cellulose, and carboxymethylcellulose sodium, and the like. These viscous bases may be used alone or in a combination of two or more.

Examples of an algefacient include l-menthol, borneol, camphor, eucalyptus oil, and the like. These algefacients may be used alone or in a combination of two or more.

Examples of a pH adjusting agent include alkalis such as sodium hydroxide, potassium hydroxide, and borax; and acids such as acetic acid, citric acid, hydrochloric acid, phosphoric acid, tartaric acid, and boric acid.

Examples of a preservative include sorbic acid or a salt thereof, benzoic acid or a salt thereof, methyl parahydroxybenzoate, ethyl parahydroxybenzoate, propyl parahydroxybenzoate, chlorobutanol, chlorhexidine gluconate, boric acid, dehydroacetic acid or a salt thereof, benzalkonium chloride, benzethonium chloride, benzyl alcohol, zinc chloride, parachlorometaxylenol, chlorocresol, phenethyl alcohol, polidronium chloride, thimerosal, polyhexamethylene biguanide, and the like. These preservatives may be used alone or in a combination of two or more.

Examples of a stabilizer include polyvinylpyrrolidone, sulfite salts, monoethanolamine, glycerin, propylene glycol, cyclodextrin, dextran, ascorbic acid, edetate salts, taurine, tocopherol, and the like. These stabilizers may be used alone or in a combination of two or more.

Examples of a surfactant include nonionic surfactants such as tyloxapol, polyoxyethylene hydrogenated castor oil, polyoxyethylene polyoxypropylene block copolymer, polyoxyethylene sorbitan fatty acid ester, and octoxynol; ampholytic surfactants such as alkyldiaminoethyl glycine, and lauryldimethylaminoacetic acid betaine; anion surfactants such as alkyl sulfate salts, N-acyl taurine salts, polyoxyethylene alkyl ether phosphate salts, and polyoxyethylene alkyl ether sulfate salts; cation surfactants such as alkylpyridinium salts and alkyl amine salts, and the like. These surfactants may be used alone or in a combination of two or more.

The concentration of these additives are appropriately set depending on the type of additive or the application of the aqueous formulation and the like.

The terms used herein, with the exception of those particularly defined, are to be employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, and shall not be construed as being limited to the Examples described herein.

EXAMPLES

Example 1: ALA Decrease Inhibitory Effect by Sodium Chloride

ALA hydrochloride salt (from COSMO OIL Co., Ltd.), sodium ferrous citrate (hereinafter SFC (from KOMATSUYA CORPORATION)), and sodium chloride (hereinafter NaCl (from Wako Pure Chemical Corporation)) were employed to prepare the following two types of aqueous solutions as samples, 10 g of each were placed in clear glass bottles, and these were stored in a thermo-hygrostat set at a temperature of 40° C. and a humidity of 75%. The ALA concentration and pH of each aqueous solution were measured before storage as well as on storage days 7, 14, 21, and 27.
1) ALA+SFC
1 g of ALA hydrochloride salt and 1 g of SFC were dissolved in ultrapure water to yield a total amount of 100 g.
2) ALA+SFC+NaCl 5 w/w %
1 g of ALA hydrochloride salt, 1 g of SFC (from KOMATSUYA CORPORATION), and 5 g of sodium chloride were dissolved in ultrapure water to yield a total amount of 100 g.

The ALA concentration was measured by the following method. All of the reagents employed were from Wako Pure Chemical Corporation.

Samples diluted 250 folds in ultrapure water were taken in 0.05 mL test tubes, 3.5 mL of reaction solution A (a mixed solution of 68.4 mM sodium chloride, 15 v/v % acetyl acetone, and 10 v/v % ethanol) and 0.5 mL of reaction solution B (3.3 w/w % formaldehyde solution) were added, these were heated in boiling water for 15 minutes, and then immediately cooled in ice. These reaction solutions were injected into HPLC, fluorescence was measured with excitation at 363 nm and fluorescence at 473 nm, and the values therefrom were used to calculate the amount of ALA by standard curve method. The column employed was Zorbax Eclipse plus C18 (1.8 μm, 4.6×5 mm, from Agilent) and the mobile phase was 2.5% acetic acid/methanol (6/4, v/v). Lacom Tester pH Meter (from AS ONE Corporation) was used for pH measurement.

Figure 1A:
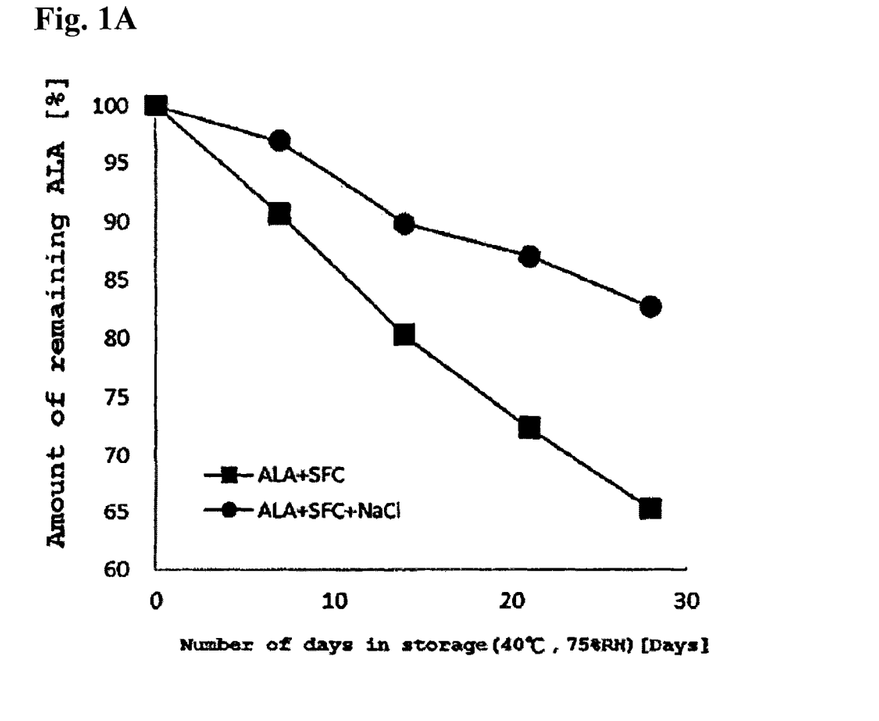
FIG. 1A is the graph showing the ALA decrease inhibitory effect of sodium chloride. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 1B:
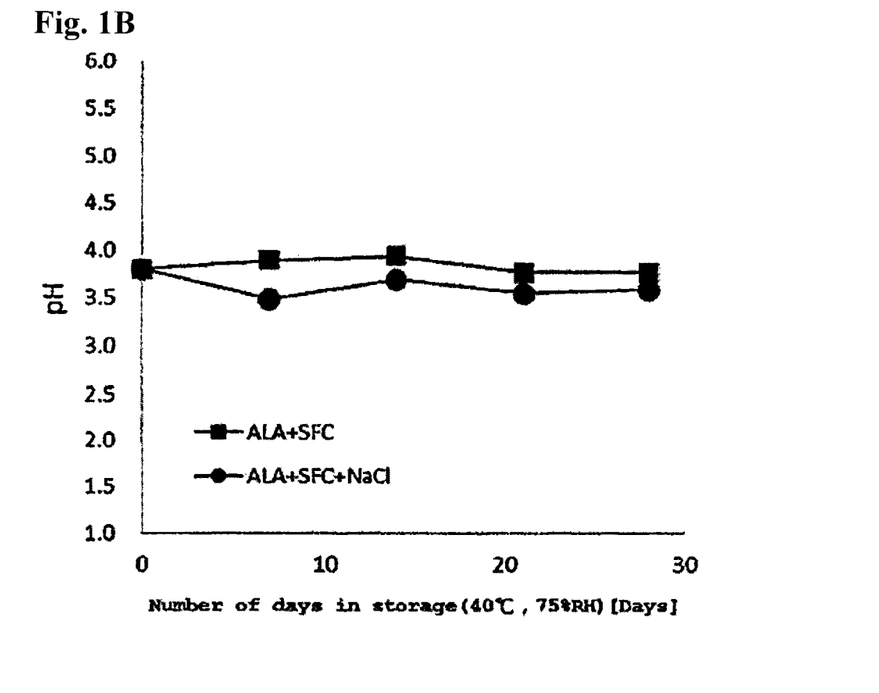
FIG. 1B shows the pH of the solution at each number of days in storage. The duration of sample storage is shown in the horizontal axis, and the pH of the sample is shown in the vertical axis.

The experiment result is shown in FIG. 1. As shown in FIG. 1A, in the sample with addition of sodium chloride, decrease of ALA was inhibited from storage day 7, and the amount of remaining ALA on storage day 27 was about 20% greater than the sample without addition of sodium chloride. Moreover, as shown in FIG. 1B, there was no difference in the pH of each sample before storage, and there was also no change in pH during the storage period. From this, it was confirmed that the ALA decrease inhibitory effect in FIG. 1A was not due to the influence of pH.

Example 2: Relationship Between Sodium Chloride Concentration and ALA Decrease Inhibitory Effect The following 4 types of aqueous solutions having differing sodium chloride concentrations were prepared as samples with a method similar to the test in Example 1, 10 g of each were placed in clear glass bottles, and these were stored in a thermo-hygrostat set at a temperature of 40° C. and a humidity of 75%. The ALA concentration and pH were measured on storage days 14 and 27, and the relationship between ALA decrease inhibitory effect and sodium chloride concentration was examined.
1) ALA+SFC
2) ALA+SFC+NaCl 1.0 w/w %
3) ALA+SFC+NaCl 2.5 w/w %
4) ALA+SFC+NaCl 5.0 w/w %

Figure 2A:
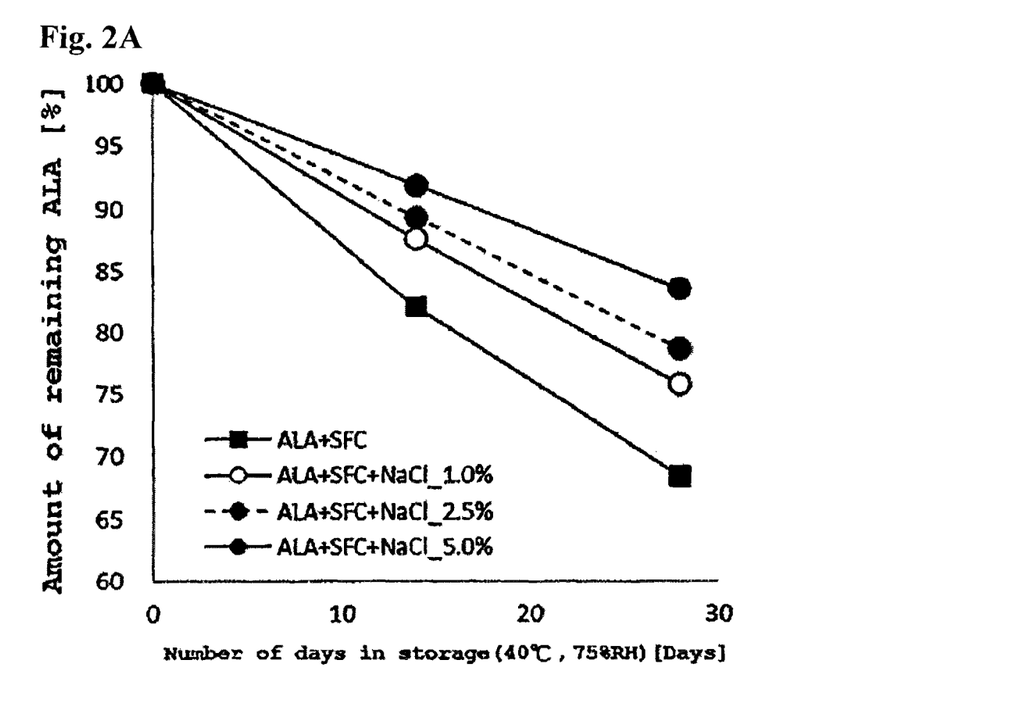
FIG. 2A shows the graph related to the relationship between the sodium chloride concentration and the ALA decrease inhibitory effect. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 2B:
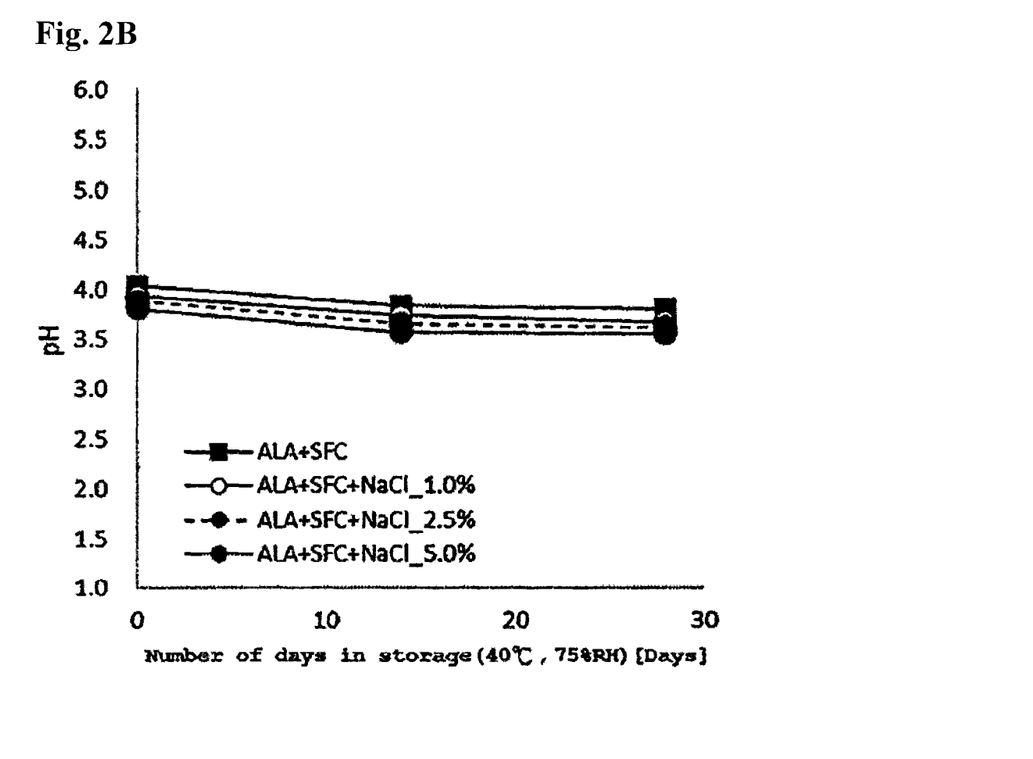
FIG. 2B shows the pH of the solution at each number of days in storage. The duration of sample storage is shown in the horizontal axis, and the pH of the sample is shown in the vertical axis.

The experiment result is shown in FIG. 2. As shown in FIG. 2A, both on storage days 14 and 27, the higher the sodium chloride concentration in the sample was, the greater the amount of remaining ALA was and the stronger the ALA decrease inhibitory effect in the aqueous solution was. Moreover, from the result of FIG. 2B, there was no difference in the pH of each sample before storage, and there was also no change in pH during the storage period. From this, it was confirmed that the ALA decrease inhibitory effect in FIG. 2A was not due to the influence of pH.

Figure 3A:
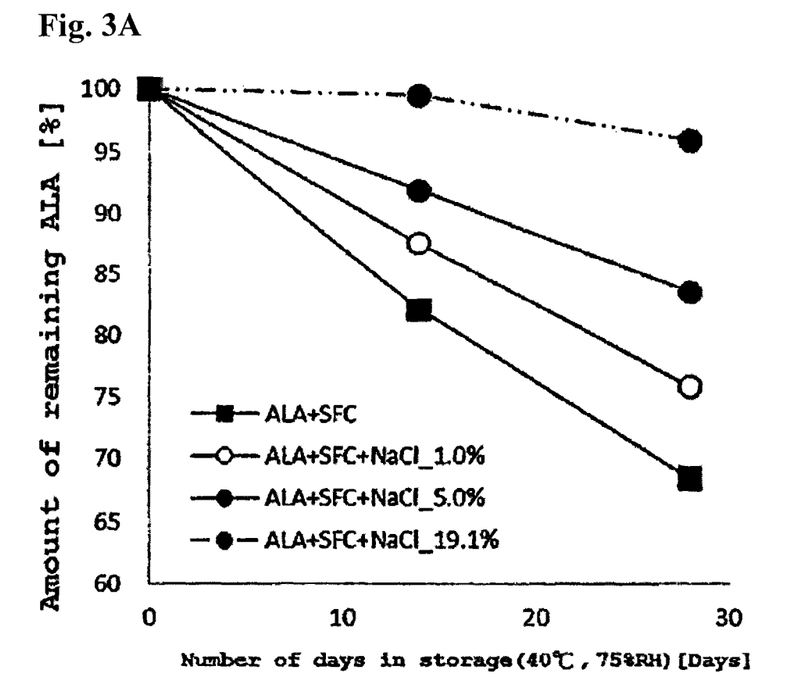
FIG. 3A is the graph related to the relationship between the sodium chloride concentration and the ALA decrease inhibitory effect. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 3B:
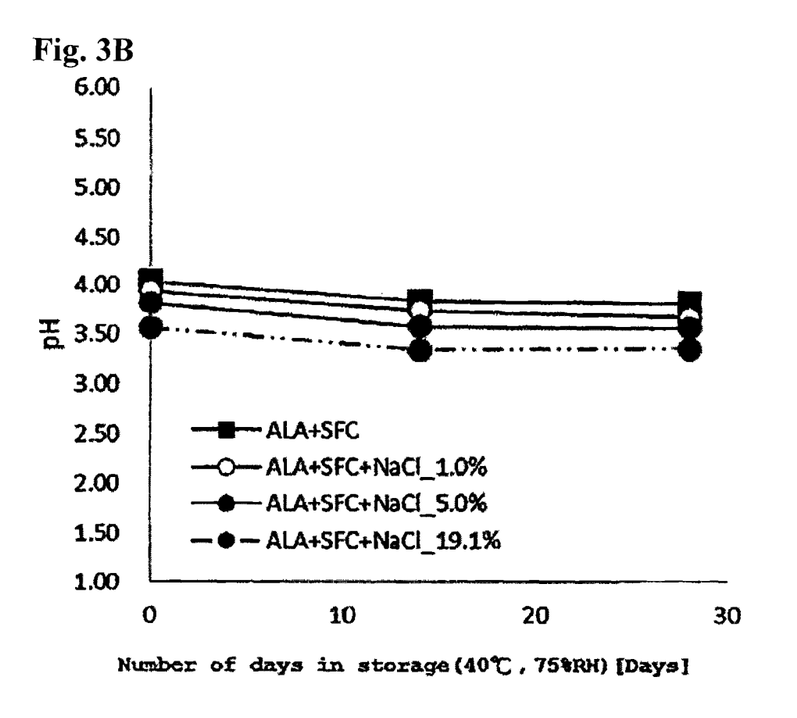
FIG. 3B shows the pH of the solution at each number of days in storage. The duration of sample storage is shown in the horizontal axis, and the pH of the sample is shown in the vertical axis.

Example 3: Relationship Between Sodium Chloride Concentration and ALA Decrease Inhibitory Effect The result of performing experiments with a sample comprising a further higher concentration of sodium chloride (19.1 w/w %) in tests similar to Example 2 is shown in FIG. 3. As shown in FIG. 3A and FIG. 3B, both on storage days 14 and 27, the higher the sodium chloride concentration in the sample was, the greater the amount of remaining ALA was and the stronger the ALA decrease inhibitory effect in the aqueous solution was.

Example 4: ALA Decrease Inhibitory Effect by Salts Other Than Sodium Chloride An aqueous solution having 1 g of ALA hydrochloride salt and 1 g of SFC dissolved in ultrapure water and an aqueous solution having potassium chloride (from Wako Pure Chemical Corporation, KCl) or sodium sulfate (from Wako Pure Chemical Corporation, Na2SO4) dissolved were mixed, adjusted to pH 4 with 1M-citrate buffer, and the total amount was made to 100 g with ultrapure water. The formulation amount of potassium chloride and sodium sulfate was as follows, and after preparation of each solution, 10 g of each were placed in clear glass bottles, and these were stored in a thermo-hygrostat set at a temperature of 40° C. and a humidity of 75%.

The ALA concentration and pH were measured on storage days 14 and 27, and the ALA decrease inhibitory effect of potassium chloride and sodium sulfate was examined.
1) ALA+SFC*control for 2), 3), and 4)
2) ALA+SFC+KCl 1.3 w/w %
3) ALA+SFC+KCl 6.4 w/w %
4) ALA+SFC+KCl 24.5 w/w %
5) ALA+SFC*control for 6), 7), and 8)

6) ALA+SFC+Na2SO4 0.8 w/w %
7) ALA+SFC+Na2SO4 4.1 w/w %
8) ALA+SFC+Na2SO4 16.2 w/w %

Figure 4A:
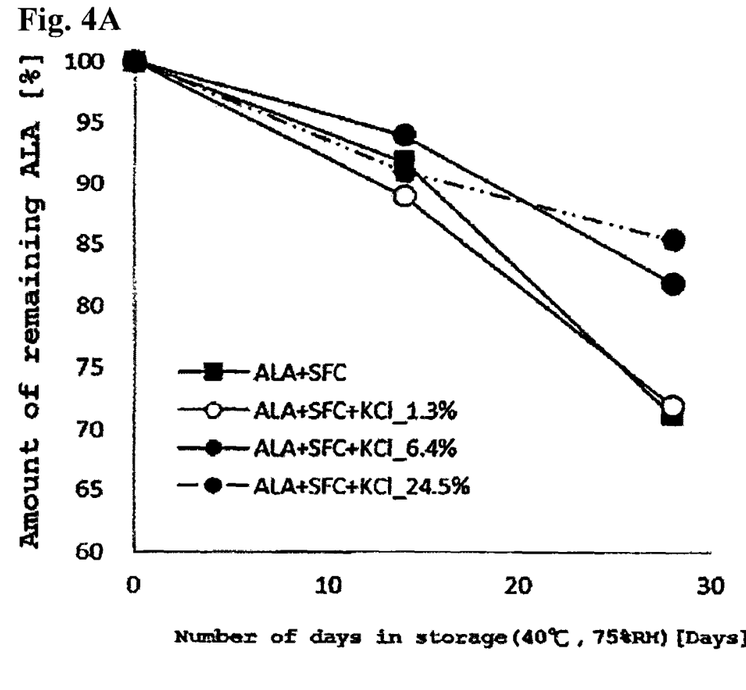
FIG. 4A is the graph showing the ALA decrease inhibitory effect of potassium chloride. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 4B:
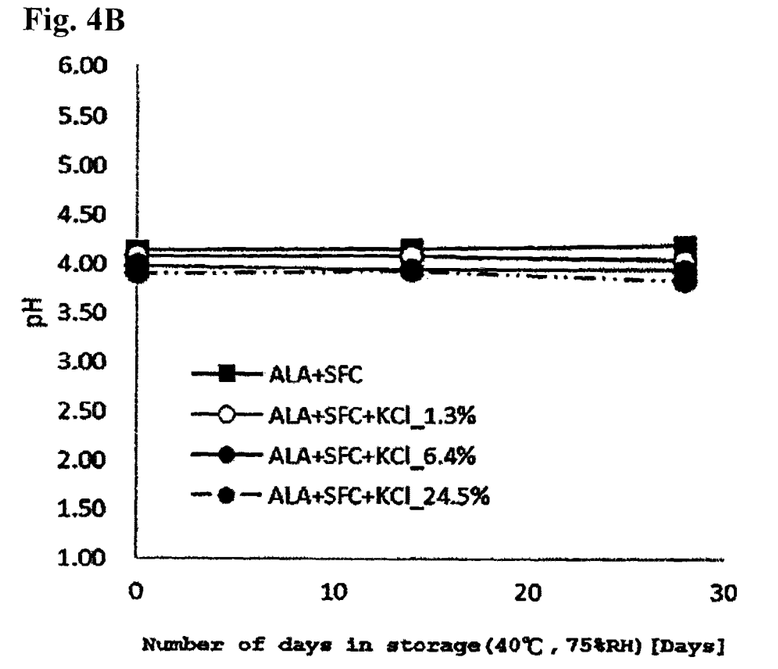
FIG. 4B shows the pH of the solution at each number of days in storage. The duration of sample storage is shown in the horizontal axis, and the pH of the sample is shown in the vertical axis.
Figure 5A:
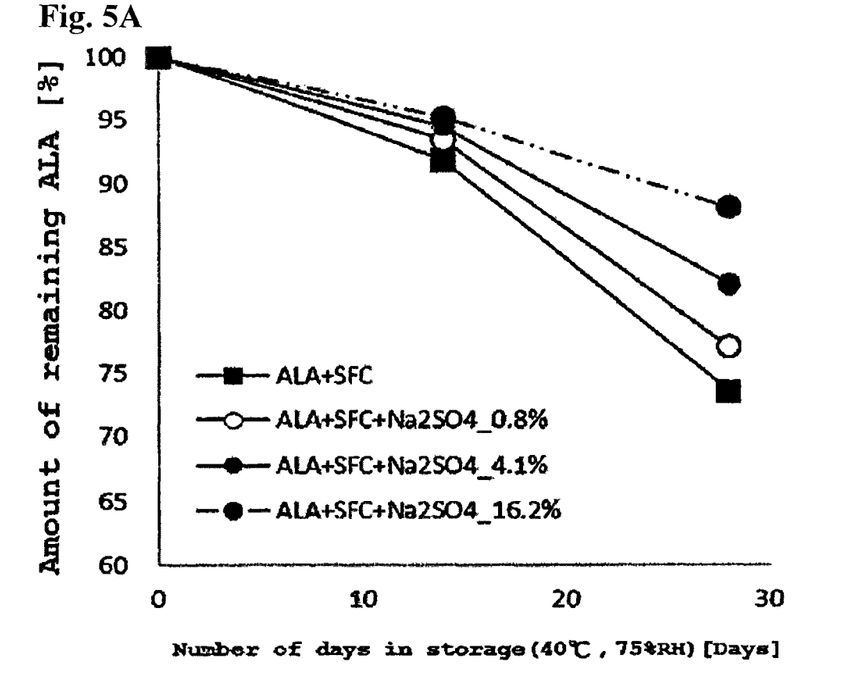
FIG. 5A is the graph showing the ALA decrease inhibitory effect of sodium sulfate. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 5B:
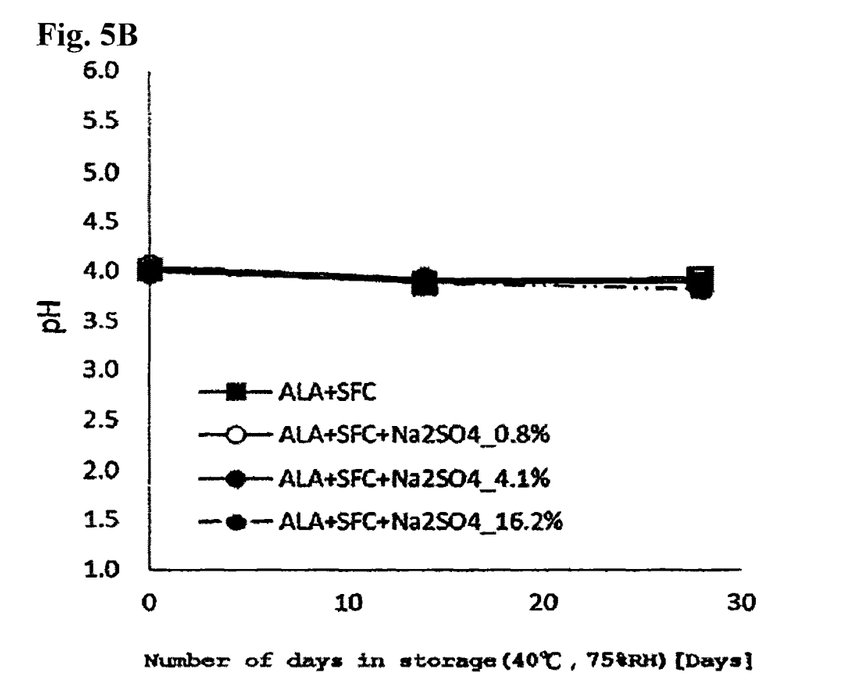
FIG. 5B shows the pH of the solution at each number of days in storage. The duration of sample storage is shown in the horizontal axis, and the pH of the sample is shown in the vertical axis.

The experiment results are shown in FIG. 4 and FIG. 5. As shown in FIG. 4A, the amount of remaining ALA on storage day 27 was about 10% greater in the samples with 6.4% or 24.5% of potassium chloride formulated compared to the sample without potassium chloride formulated. Similarly in FIG. 5A, the amount of remaining ALA on storage day 27 was also greater in samples with sodium sulfate formulated compared to the sample without sodium sulfate formulated. From the above, it was confirmed that ALA decrease inhibitory effect is obtained even when a salt other than sodium chloride was added to the sample. Moreover, as shown in FIG. 4B and FIG. 5B, there was no difference in the pH of each sample before storage, and there was also no change in pH during the storage period. From this, it was confirmed that the ALA decrease inhibitory effect shown in FIG. 4A and FIG. 5A was not due to the influence of pH.

Example 5: ALA Decrease Inhibitory Effect of Salts on ALA Phosphate Salt

ALA phosphate salt (from COSMO OIL Co., Ltd.), sodium ferrous citrate (hereinafter SFC, from KOMATSUYA CORPORATION), sodium chloride (hereinafter NaCl, from Wako Pure Chemical Corporation), potassium chloride (hereinafter KCl, from Wako Pure Chemical Corporation), and sodium sulfate (hereinafter $Na_2SO_4$, from Wako Pure Chemical Corporation) were employed to prepare the following 4 types of aqueous solutions as samples. After adjusting the pH to pH 4 with 1M-citrate buffer, 20 g of each were placed in clear glass bottles, and these were stored in a thermo-hygrostat set at a temperature of 40° C. and a humidity of 75%.

The ALA concentration and pH of each aqueous solution were measured before storage as well as on storage days 14 and 28, and it was verified whether addition of salts inhibits the decrease in the amount of ALA also in the case of ALA phosphate salt. Note that ALA concentration and pH were measured with a method similar to previous Examples. Moreover, unless specifically described, all of the reagents employed were from Wako Pure Chemical Corporation.

1) ALA+SFC 1.37 g of ALA phosphate salt and 1.0 g of SFC were dissolved in ultrapure water to yield a total amount of 100 g.

2) ALA+SFC+NaCl 5.0 w/w %

1.37 g of ALA phosphate salt, 1.0 g of SFC, and 5.0 g of NaCl were dissolved in ultrapure water to yield a total amount of 100 g.

3) ALA+SFC+KCl 6.4 w/w %

1.37 g of ALA phosphate salt, 1.0 g of SFC, and 6.4 g of KCl were dissolved in ultrapure water to yield a total amount of 100 g.

4) ALA+SFC+$Na_2SO_4$ 4.1 w/w %

1.37 g of ALA phosphate salt, 1.0 g of SFC, and 4.1 g of $Na_2SO_4$ were dissolved in ultrapure water to yield a total amount of 100 g.

Figure 6A:
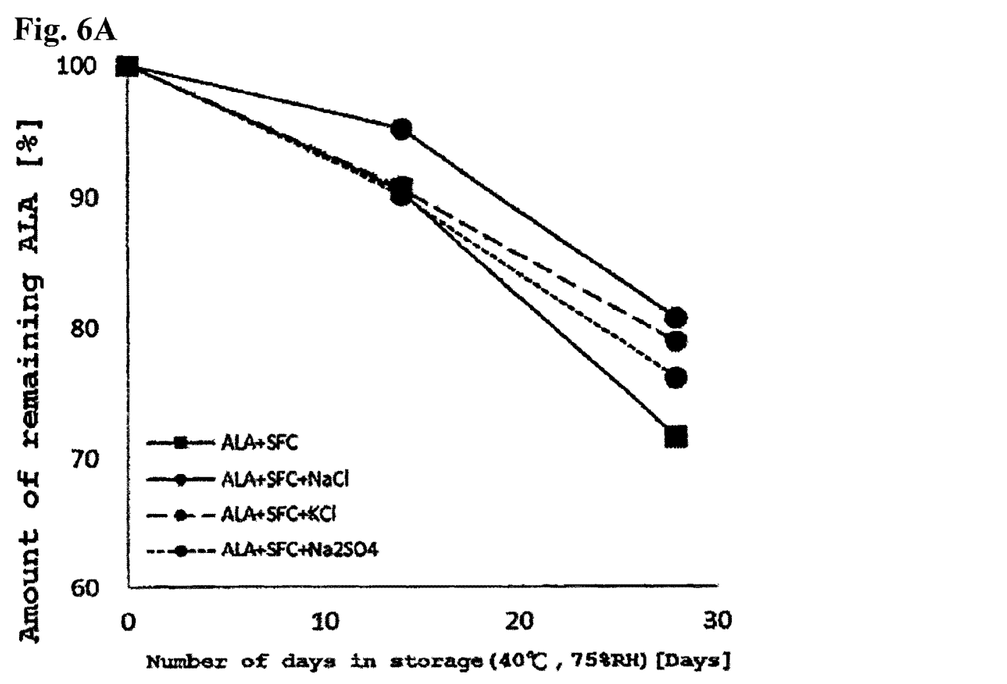
FIG. 6A is the graph showing the ALA decrease inhibitory effect of salts on ALA phosphate salt. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 6B:
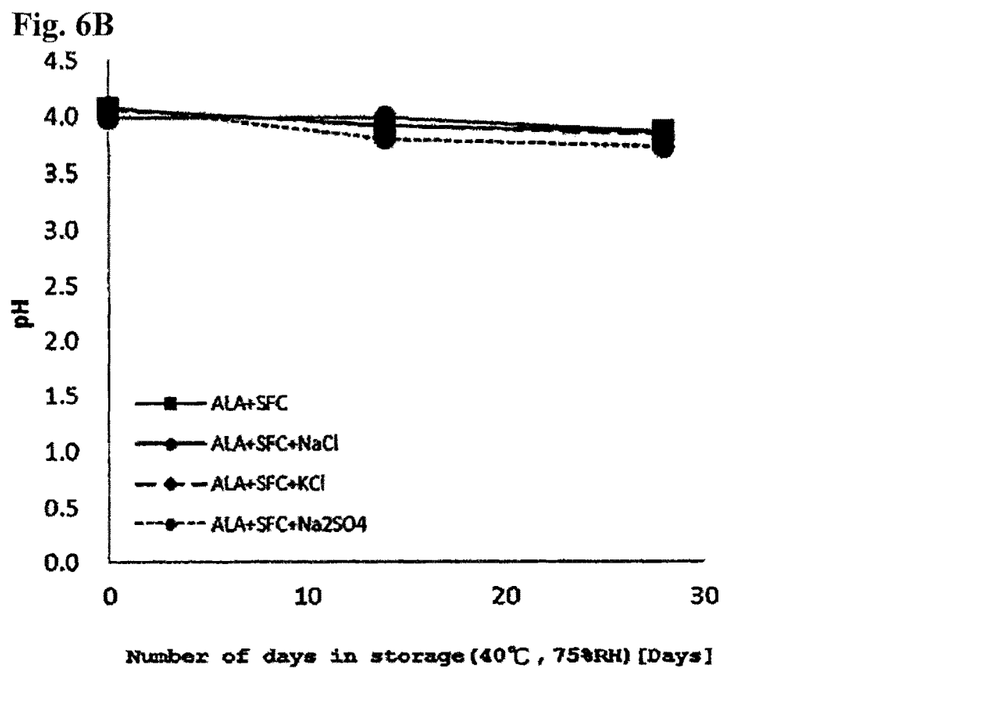
FIG. 6B shows the pH of the solution at each number of days in storage. The duration of sample storage is shown in the horizontal axis, and the pH of the sample is shown in the vertical axis.

The experiment result is shown in FIG. 6. As shown in FIG. 6A, the amount of remaining ALA on storage day 28 for the samples with addition of NaCl, KCl, and $Na_2SO_4$ was approximately 9%, 7%, and 4% greater than the samples without addition of salts, respectively. From this result, ALA decrease inhibitory effect due to addition of salts was confirmed even when ALA hydrochloride salt was altered to ALA phosphate salt. Moreover, as shown in FIG. 6B, there was no difference in the pH of each sample before storage, and there was also no change in pH during the storage period. From this, it was confirmed that the ALA decrease inhibitory effect in FIG. 6A was not due to the influence of pH.

Example 6: ALA Decrease Inhibitory Effect of Salts on ALA+Iron DTPA Aqueous Solution ALA hydrochloride salt and iron diethylenetriaminepentaacetate 50% solution (hereinafter "iron DTPA solution", from CHELEST CORPORATION), as well as NaCl were employed to prepare the following 3 types of aqueous solutions having differing NaCl concentrations as samples. After adjusting these to pH 4 with 1M-citrate buffer, 20 g of each were placed in clear glass bottles, and these were stored in a thermo-hygrostat set at a temperature of 40° C. and a humidity of 75%. The ALA concentration and pH of samples were measured before storage as well as on storage days day 28, and it was verified whether the ALA decrease inhibitory effect due to addition of salts is obtained also in the case of ALA aqueous solution with addition of an iron preparation other than SFC.

1) ALA+iron DTPA

To ultrapure water having dissolved 1.0 g of ALA hydrochloride salt, 1.82 g of iron DTPA solution was added to yield a total amount of 100 g.

2) ALA+iron DTPA+NaCl 5.0 w/w %

To ultrapure water having dissolved 1.0 g of ALA hydrochloride salt and 5.0 g of NaCl, 1.82 g of iron DTPA solution was added to yield a total amount of 100 g.

3) ALA+iron DTPA+NaCl 20.0 w/w %

To ultrapure water having dissolved 1 g of ALA hydrochloride salt and 20.0 g of NaCl, 1.82 g of iron DTPA solution was added to yield a total amount of 100 g.

Figure 7A:
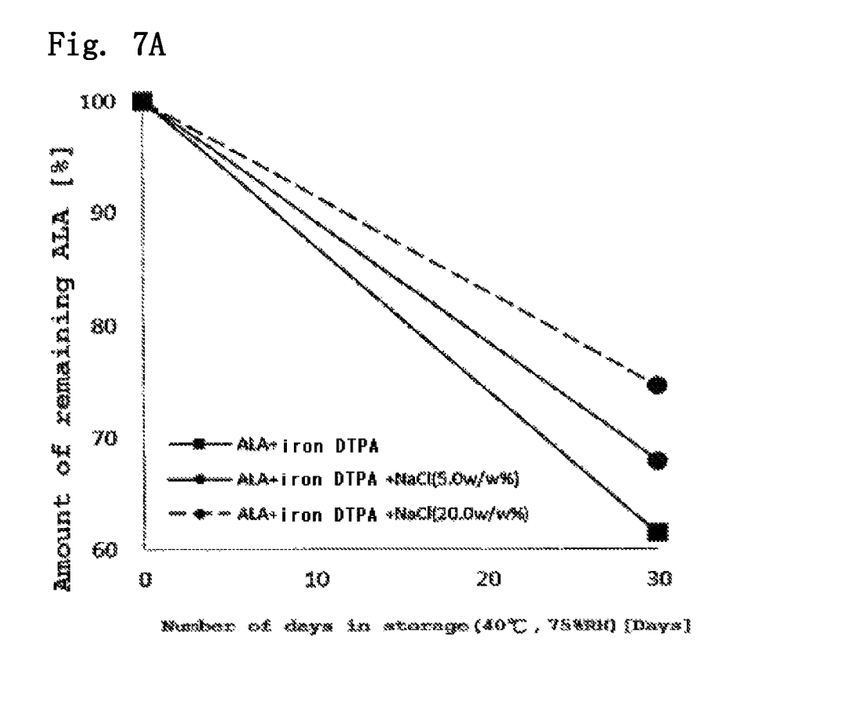
FIG. 7A is the graph showing the ALA decrease inhibitory effect of salts on ALA+iron DTPA aqueous solution. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 7B:
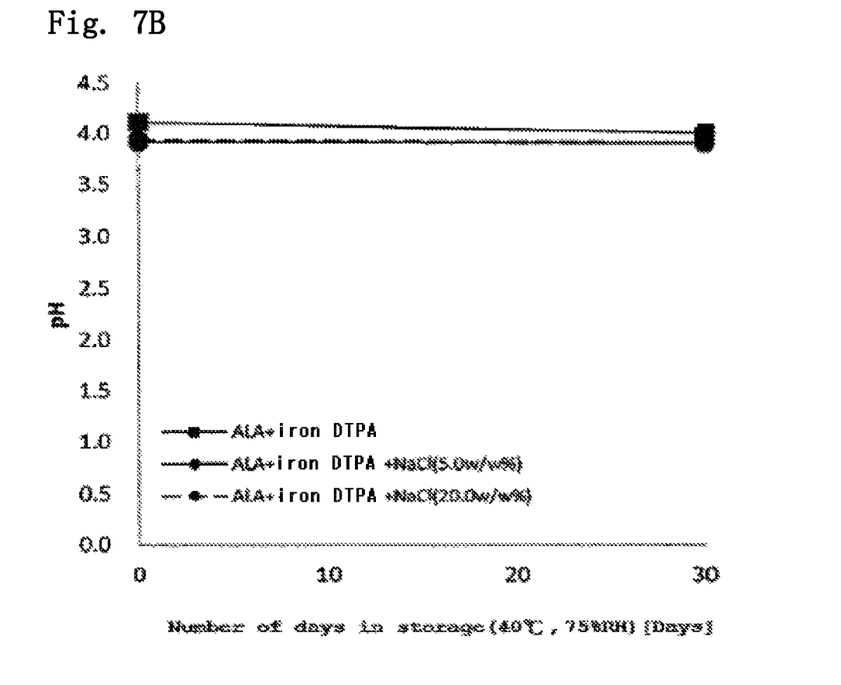
FIG. 7B shows the pH of the solution at each number of days in storage. The duration of sample storage is shown in the horizontal axis, and the pH of the sample is shown in the vertical axis.

The experiment result is shown in FIG. 7. As shown in FIG. 7A, the higher the NaCl concentration in the sample was, the greater the amount of remaining ALA was and the stronger the ALA decrease inhibitory effect in the aqueous solution was. From this result, ALA decrease inhibitory effect due to addition of salts was confirmed even when the iron preparation was iron DTPA. Moreover, as shown in FIG. 7B, there was no difference in the pH of each sample before storage, and there was also no change in pH during the storage period. From this, it was confirmed that the ALA decrease inhibitory effect in FIG. 7A was not due to the influence of pH.

Example 7: ALA Decrease Inhibitory Effect of Salts on ALA Aqueous Solution (No Addition of Iron Preparation)

Aqueous solutions with addition of 4 types of salts were prepared with the following method as samples, and after adjusting to pH 4 with 1M-citrate buffer, 20 g each of each solution were placed in clear glass bottles, and these were stored in a thermo-hygrostat set at a temperature of 40° C. and a humidity of 75%. The ALA concentration and pH were measured before storage as well as on storage days 28, 86, and 231, and it was verified whether the ALA decrease inhibitory effect due to addition of salts is obtained also in the case of the ALA aqueous solution without addition of an iron preparation.

1) ALA 1.0 g of ALA hydrochloride salt was dissolved in ultrapure water to yield a total amount of 100 g.

2) ALA+NaCl 5.0 w/w %

1.0 g of ALA hydrochloride salt and 5.0 g of NaCl were dissolved in ultrapure water to yield a total amount of 100 g.

3) ALA+KCl 6.4 w/w %

1.0 g of ALA hydrochloride salt and 6.4 g of KCl were dissolved in ultrapure water to yield a total amount of 100 g.

4) ALA+Na$_2$SO$_4$ 4.1 w/w %

1.0 g of ALA hydrochloride salt and 4.1 g of Na$_2$SO$_4$ were dissolved in ultrapure water to yield a total amount of 100 g.

Figure 8A:
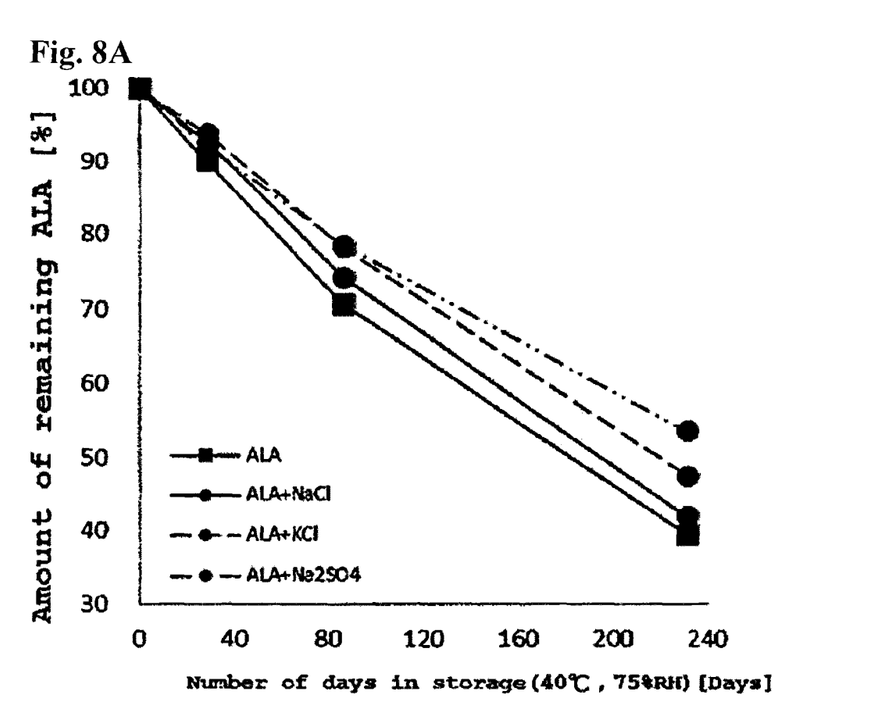
FIG. 8A is the graph showing the ALA decrease inhibitory effect of salts on ALA aqueous solution (no addition of iron preparation). The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 8B:
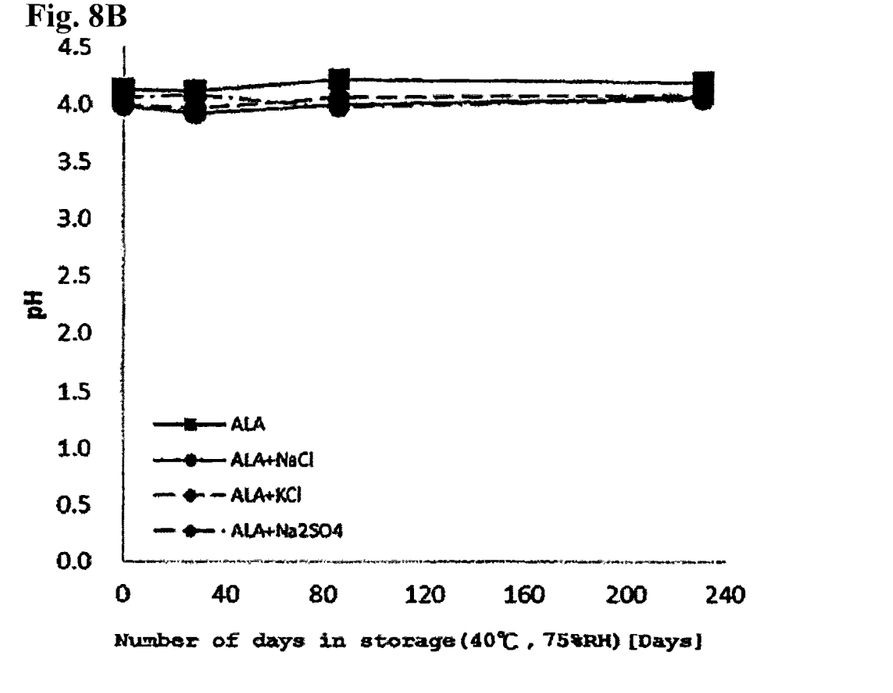
FIG. 8B shows the pH of the solution at each number of days in storage. The duration of sample storage is shown in the horizontal axis, and the pH of the sample is shown in the vertical axis.

The experiment result is shown in FIG. 8. As shown in FIG. 8A, the amount of remaining ALA on storage day 231 was at a similar level for the sample with addition of NaCl with the sample without addition of salts, but the samples with addition of KCl and Na$_2$SO$_4$ were approximately 8% and 14% greater than the sample without addition of salts, respectively. From the above, ALA decrease inhibitory effect due to addition of salts was confirmed also in the case of the ALA aqueous solution without addition of an iron preparation. Moreover, as shown in FIG. 8B, there was no difference in the pH of each sample before storage, and there was also no change in pH during the storage period. From this, it was confirmed that the ALA decrease inhibitory effect in FIG. 8A was not due to the influence of pH.

Example 8: ALA Decrease Inhibitory Effect of Multiple Types of Salts on ALA+SFC Aqueous Solution ALA+SFC aqueous solutions with addition of 3 types of salts (NaCl, KCl, and Na$_2$SO$_4$) or NaCl were prepared with the following method as samples, and after adjusting to pH 4 with 1M-citrate buffer, 20 g each of each solution were placed in clear glass bottles, and these were stored in a thermo-hygrostat set at a temperature of 40° C. and a humidity of 75%. The ALA concentration and pH were measured before storage as well as on storage days day 28, and it was verified whether the ALA decrease inhibitory effect is improved by adding multiple types of low concentration salts to increase the total amount of salts added.

1) ALA+SFC 1.0 g of ALA hydrochloride salt and 1.0 g of SFC were dissolved in ultrapure water to yield a total amount of 100 g.

2) ALA+SFC+NaCl 0.5 w/w %

1.0 g of ALA hydrochloride salt, 1.0 g of SFC, and NaCl 0.5 g were dissolved in ultrapure water to yield a total amount of 100 g.

3) ALA+SFC+NaCl 1.5 w/w %

1.0 g of ALA hydrochloride salt, 1.0 g of SFC, and NaCl 1.5 g were dissolved in ultrapure water to yield a total amount of 100 g.

4) ALA+SFC+NaCl 0.5 w/w %+KCl 0.6 w/w %+Na$_2$SO$_4$ 0.4 w/w % (total concentration of 3 types of salts added at 1.5 w/w %)

1.0 g of ALA hydrochloride salt, 1.0 g of SFC, NaCl 0.5 g, KCl 0.6 g, and 0.4 g of Na$_2$SO$_4$ were dissolved in ultrapure water to yield a total amount of 100 g.

Figure 9A:
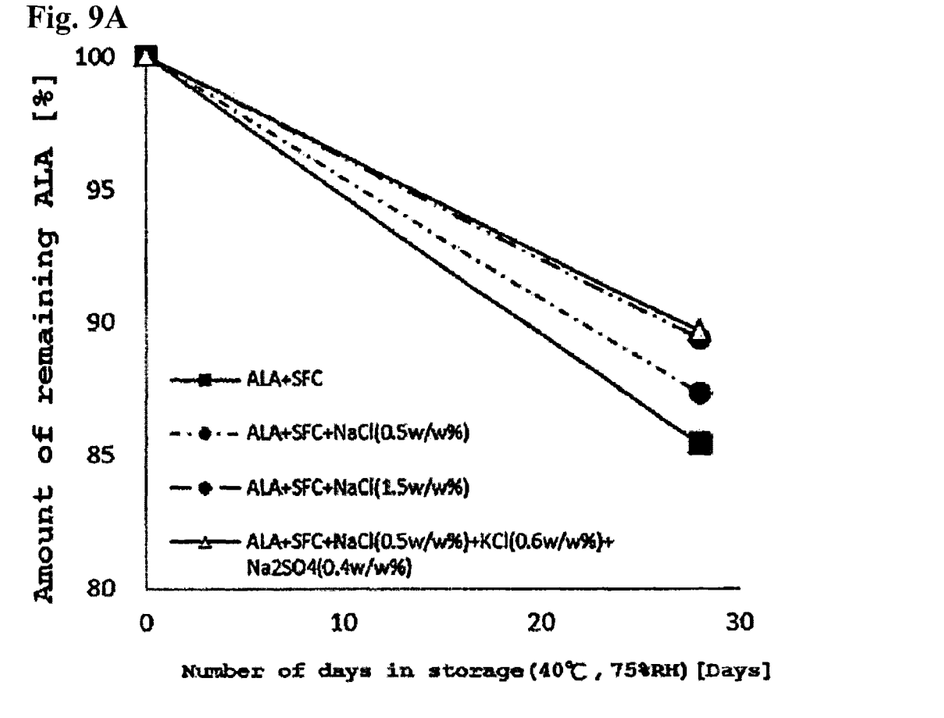
FIG. 9A is the graph showing the ALA decrease inhibitory effect of multiple types of salts on ALA+SFC aqueous solution. The duration of sample storage is shown in the horizontal axis, and the amount of remaining ALA (the percentage of ALA concentration when setting the ALA concentration in the aqueous solution immediately after preparing the samples as 100%) is shown in the vertical axis.
Figure 9B:
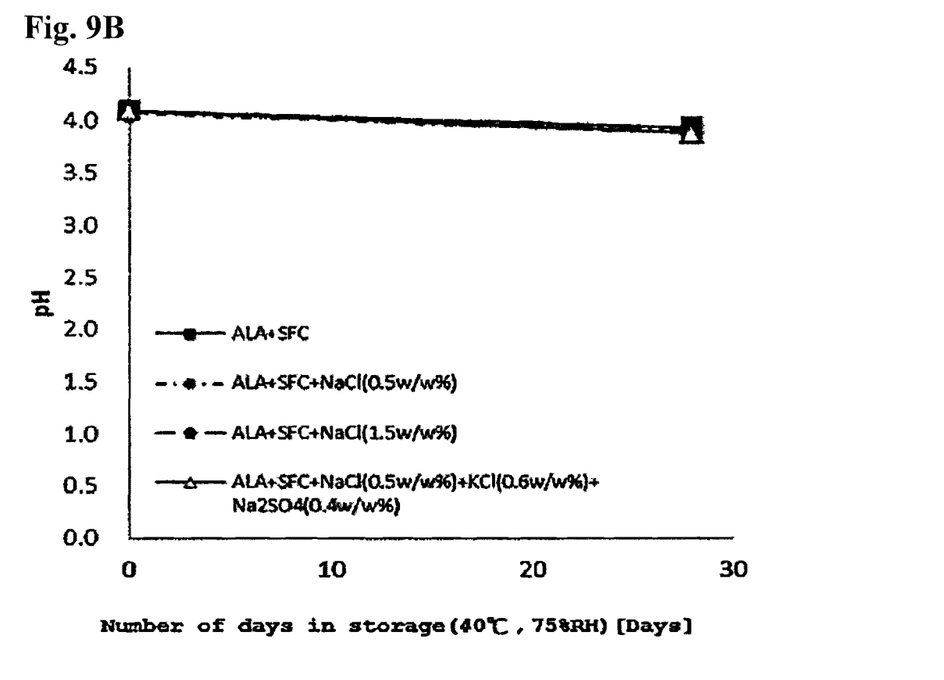
FIG. 9B shows the pH of the solution at each number of days in storage. The duration of sample storage is shown in the horizontal axis, and the pH of the sample is shown in the vertical axis.

The experiment result is shown in FIG. 9. As shown in FIG. 9A, the amount of remaining ALA on storage day 28 of the sample with addition of 3 types of salts at a total of 1.5% was at a similar level with the sample with addition of NaCl at 1.5%, making it approximately 5% greater than the sample without addition of salt. From the above, it was shown that even when the concentration of each of the salts is low, ALA decrease inhibitory effect is improved if the total amount of salts added increases. Moreover, as shown in FIG. 9B, there was no difference in the pH of each sample before storage, and there was also no change in pH during the storage period. From this, it was confirmed that the ALA decrease inhibitory effect in FIG. 9A was not due to the influence of pH.

The invention claimed is:

1. An aqueous formulation comprising:
a compound shown by the following Formula (I):

[Chemical Formula 1]

(I)

wherein R$^1$ represents a hydrogen atom or an acyl group, and R$^2$ represents a hydrogen atom, a linear or branched alkyl group, a cycloalkyl group, an aryl group, or an aralkyl group) or a salt thereof and
an iron compound,
wherein the composition further comprises:
2.5-30% by weight of salts,
said salts are sodium salts or potassium salts, and
the pH of said aqueous formulation is 2-8.

2. The aqueous formulation according to claim 1, wherein in said Formula (I), R$^1$ is selected from the group consisting of a hydrogen atom, an alkanoyl group having 1-8 carbons, and an aroyl group having 7-14 carbons, and R$^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

3. The aqueous formulation according to claim 1, characterized in that in said Formula (I), R$^1$ and R$^2$ are hydrogen atoms.

4. The aqueous formulation according to claim 1, wherein the ratio between the amount of said iron compound (mol) and the amount of the compound shown by said Formula (I) (mol) (iron compound/the compound shown by Formula (I)) contained in said aqueous formulation is 0.01-100.

5. The aqueous formulation according to claim 1, wherein:
said sodium salt is sodium chloride, sodium sulfate, sodium carbonate, or sodium acetate, and
said potassium salt is potassium chloride, potassium acetate, or potassium carbonate.

6. The aqueous formulation according to claim 1, wherein said iron compound is one or two or more compounds selected from the group consisting of ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron sodium succinate citrate, heme iron, iron dextran, triethylenetetramine iron, lactoferrin iron, transferrin iron, sodium iron chlorophyllin, ferritin iron, saccharated iron oxide, and iron glycine sulfate.

7. The aqueous formulation according to claim 1, wherein the pH of said aqueous formulation is 4-7.5.

8. The aqueous formulation according to claim 7, wherein the pH of said aqueous formulation is 5-7.

9. The aqueous formulation according to claim 1, wherein said aqueous formulation is in a form of an aqueous solution, a jelly, a gel, a cream, or an ointment.

* * * * *